United States Patent [19]

Yukl

[11] Patent Number: 4,912,982
[45] Date of Patent: Apr. 3, 1990

[54] NON-PERTURBING CAVITY METHOD AND APPARATUS FOR MEASURING CERTAIN PARAMETERS OF FLUID WITHIN A CONDUIT

[75] Inventor: Tex Yukl, Baker, Oreg.

[73] Assignee: Spatial Dynamics, Ltd., Baker, Oreg.

[21] Appl. No.: 256,308

[22] Filed: Oct. 11, 1988

[51] Int. Cl.⁴ ..................... G01F 1/708; G01N 22/00; G01R 27/04
[52] U.S. Cl. ................................. 73/861.05; 324/636; 73/861.08
[58] Field of Search ........................ 73/861.08, 861.05; 324/58 C, 58.5 C; 604/65; 128/DIG. 13

[56] References Cited

U.S. PATENT DOCUMENTS

| | | |
|---|---|---|
| 4,234,844 | 11/1980 | Yukl . |
| 4,318,108 | 3/1982 | Yukl . |
| 4,651,085 | 3/1987 | Sakurai et al. ................. 324/58.5 C |
| 4,751,476 | 6/1988 | Meijer ......................... 128/DIG. 13 |

Primary Examiner—Herbert Goldstein
Attorney, Agent, or Firm—Kolisch, Hartwell & Dickinson

[57] ABSTRACT

A non-perturbing cavity method and apparatus for measuring parameters, such as dielectric constant and flow rate, of fluid within a conduit. A bidirectionally radiating lens directs energy toward a defined length of such a conduit, and toward a receiver at a receiving site on the opposite side of the lens. The receiver produces a signal whose voltage amplitude conditions are directly interpretable to indicate such parameters.

8 Claims, 2 Drawing Sheets

NON-PERTURBING CAVITY METHOD AND APPARATUS FOR MEASURING CERTAIN PARAMETERS OF FLUID WITHIN A CONDUIT

BACKGROUND AND SUMMARY OF THE INVENTION

This invention pertains to a method and to an apparatus for measuring certain parameters, such as dielectric constant and flow rate, of fluid within a conduit.

While the invention has significant utility in a wide field of applications, the same is disclosed herein in connection with a medical application wherein it has been found to offer particular initial utility. More specifically, the method and apparatus of the invention are described in the setting of monitoring the intravenous supply of fluid to a patient in a hospital, or the like.

There are many instances where it is both desirable and important to be able to monitor certain characteristics of fluid which is flowing in a conduit. One setting, familiar to many people, is that where certain fluids are being introduced intravenously into a patient. In this setting, it is important for attendant medical personnel to know, for example, that there is no chemical change occurring in the prescribed fluid, as for example could occur if another non-prescribed fluid were inadvertently introduced into the system, that blood were to back up into the system, or that air bubbles have been introduced into the system. Rate of flow can also be an important matter to watch.

A general object of the present invention is to provide a highly-accurate non-perturbing method and apparatus for monitoring such fluid parameters within a conduit which forms part of the fluid-flow system.

More particularly, an object of the invention is to provide such a method and apparatus which employs a bidirectionally radiating lens which forms part of a very high-Q resonant cavity, with a defined length of conduit, which carries the fluid of interest, disposed on one side of the lens, wherein the conduit length is subjected to microwave radiation. The invention further employs a receiving electrode disposed on the opposite side of the lens, wherein voltage-amplitude signal levels are monitoribie. Still another object of the invention is to provide a method and apparatus of the type generally outlined which is easily used.

The method and apparatus of the invention utilize information derived from what is referred to herein as a defined, or predetermined, length of conduit, which conduit is substantially transparent to microwave-frequency radiation. This defined length of conduit is placed in a preferred position on one side of the lens in order to maximize signal-to-noise ratio. The amplitude of voltage signals developed in the receiving electrode are, through pre-system calibration, directly readable to provide information about the dielectric constant of fluid flowing in the system, and also to provide fluid-flow-rate information. Two different kinds of receiving electrodes are disclosed herein, each of which promotes a slightly different way of deriving flow-rate information. The apparatus and method are non-perturbing in the sense that no transducer is introduced directly into the fluid stream.

Those skilled in the art will recognize that information about the dielectric constant of fluid flowing within a fluid-flow system is directly interpretable to indicate the nature, or material characteristics, of the fluid flowing in the system, given the fact that, in any particular application, the user will know, generally, the different categories of fluids which could be expected to appear in the system.

These and other objects and advantages which are attained by the invention will become more fully apparent as the description which now follows is read in conjunction with the accompanying drawings.

DETAILED DESCRIPTION OF THE INVENTION

Figure 1:
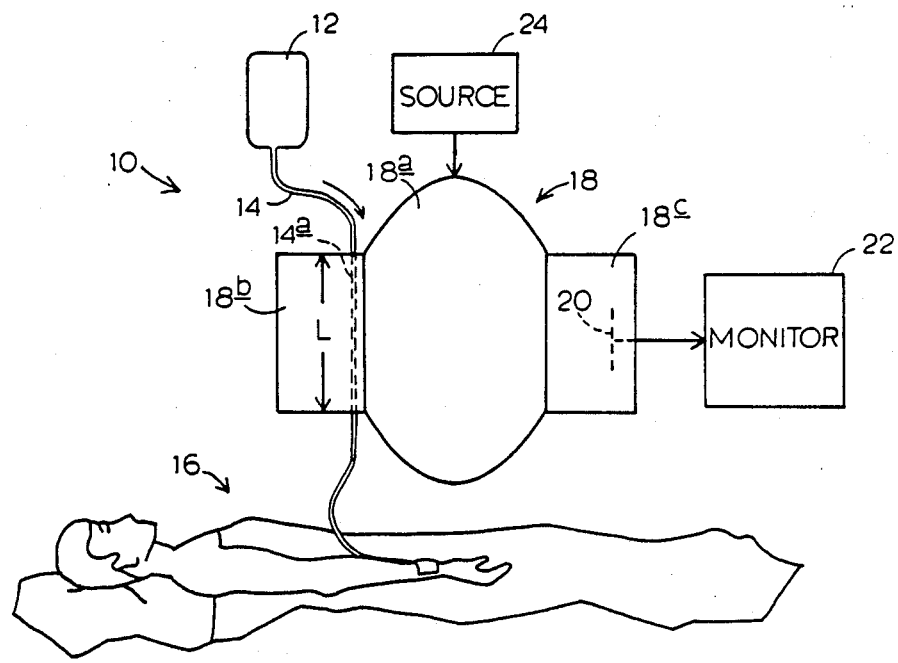
FIG. 1 is a simplified schematic view illustrating fluid-parameter monitoring system employing apparatus constructed in accordance with the present invention, illustrated in a condition for monitoring fluid-flow parameters vis-a-vis the intravenous irrigating of a patient.

Turning attention now to the drawings, and referring first of all to FIG. 1, indicated generally at 10 is a system including what is referred to herein as non-perturbing apparatus for monitoring certain selected parameters of fluid flowing in a conduit. In the particular system which is illustrated in this figure, the apparatus of the invention is being employed to monitor the flow of intravenous fluid from a bottle 12 through a conduit structure 14 into the arm of a patient shown generally at 16.

The non-perturbing apparatus of the invention includes a high-Q (about 2700) resonant cavity 18, which may be thought of as including three cavity sections, or regions, 18a, 18b, 18c, which cooperate in a manner that will be explained shortly, a receiving element, or electrode, 20, also referred to herein as a responsive means, contained as will be explained within cavity section 18c, and monitor circuitry 22 which is also referred to herein as a generating means for producing desired output data.

A power source for energizing the system at the chosen operating frequency, which herein is 1624-MHz, is shown at 24, and is coupled, as will be more fully explained, to cavity section 18a and to monitor circuitry 22. The monitor circuitry, in addition, is coupled, as is indicated in FIG. 1, to electrode 20.

Forming a portion of previously mentioned conduit structure 14 is what is referred to herein as a defined length 14a of conduit, having a length shown at L, extending diametrically through cavity section 18b. This defined length of conduit may either be a section of a single homogenous conduit structure which is suitably extended through cavity section 18b, or it may be an independent, fixed-length conduit section which is permanently installed in section 18b, with its ends suitably coupled to permit intravenous flow such as that illustrated in FIG. 1.

Before describing the apparatus of the invention in greater detail, a general description of its operation may, at this point, be useful.

Cavity section 18a, with the system energized, functions as a radiator means, and more specifically, as a bidirectionally radiating lens, which directs energy toward two focal points which are located on opposite active sides of this lens into cavity sections 18b, 18c. A typical input power level is about 2-milliwatts (RMS).

With the system operating, monitor circuitry 22 monitors, the voltage of a resulting output signal emanating from electrode 20. This signal is composed of the incident wave from the driven element in lens 18a algebraically added to the reflected wave arriving from the monitored reference 18b of which the integrated conduit is part. With the apparatus operating and calibrated, changes in the dielectric constant of fluid within the defined length of conduit produces related changes in the voltage level of a signal output by electrode 20. Monitor circuitry 22 produces from this a suitable output indication, which may be presented in any one of a variety of well known forms, which is a direct indication of the dielectric-constant parameter of the fluid within the defined conduit length. Any change in the dielectric constant character of fluid within this conduit length which could indicate one of the undesirable circumstances mentioned earlier is directly indicated by the monitor circuitry.

If one desires to determine flow rate in the defined length of conduit, fluid having a suitably different dielectric constant than that "currently" being monitored is injected into the system upstream from length 14a, and what might be thought of as the traveling wave front of this injection produces, as will shortly be more fully explained, time-spaced peaks in the signal coming from electrode 20. These peaks relate to the points in time that the wave front first entered cavity section 18b and later exited the cavity section. Naturally, with length L known, and the time "distance" between these peaks acquired, flow rate is directly determined.

Figure 2:
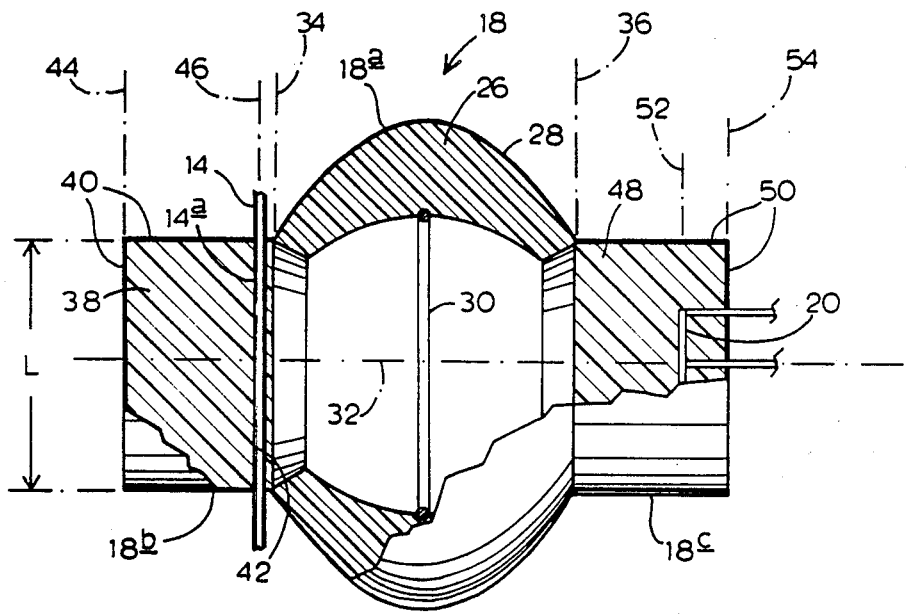
FIG. 2 is an enlarged fragment of the system of FIG. 1, with portions broken away to illustrate details of construction of a high-Q resonant cavity, including a bidirectionally radiating lens, and on opposite sides thereof, a cavity region defining a sample zone containing a defined length of conduit wherein fluid-flow is monitoribie, and another cavity region defining a monitoring zone containing a receiving electrode (one embodiment).
Figure 3:
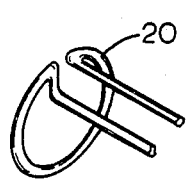
FIGS. 3 and 4 are isolated (removed from structure) perspective views illustrating two different kinds of receiving electrodes—that shown in FIG. 3 being the one which is illustrated in FIG. 2, and that shown in FIG. 4 being modified in form.

Shifting attention now to FIGS. 2 and 3, along with FIG. 1, FIG. 2 illustrates in greater detail the structure in the system including and immediately associated with cavity 18.

As has been mentioned, the central portion 18a of cavity 18 takes the form of a bidirectionally radiating lens. The construction and operation of such a lens are fully described and discussed in two U.S. Patents previously issued to me, namely, U.S. Pat. No. 4,318,108 for BIDRIECTIONALLY FOCUSING ANTENNA, issued Mar. 2, 1982, and U.S. Pat. No. 4,234,844 for ELECTROMAGNETIC NONCONTACTING MEASURING APPARATUS, issued Nov. 18, 1980. The disclosure contents of those two patents are hereby incorporated herein by reference.

In accordance with the teachings of these two patents, lens 18a is formed with a polystyrene body 26, having a dielectric constant of about 2.51, and formed with the specific shape shown herein and discussed in the two patents. The precise dimensions for this lens are calculated in accordance with the teachings of those patents, and with the understanding that the chosen operating frequency herein is that expressed earlier. The outer surface of body 26 is coated with a suitable conductive layer 28. Disposed centrally between the opposite active sides of the lens (the left and right sides therein in. FIG. 2) is a central, circular, driven ring, or element, 30. This element is driven by source 24 at diametrically opposed points on the element which lie along a line which is normal to the plane of FIG. 2, and which intersects the lens' central axis 32.

As will be appreciated from the teachings of the two referenced patents, lens 18a is a body of revolution centered about axis 32. The lens has circular openings at its opposite active sides, which openings each has a diameter substantially equaling dimension L. The overall length of lens 18a (between planes 34, 36 along axis 32) is slightly more than $0.25\lambda$, where $\lambda$ is the operating wave length (at the frequency described) within a transmission medium which has a dielectric constant of about 2.51.

Cavity section 18b is cylindrical, and includes a central, solid core 38 of polystyrene, an outer conductive layer 40, and a diametrically extending passage 42 which extends in the plane of FIG. 2 immediately adjacent the left active side of lens 18a. Passage 42, in the apparatus now being described, permanently receives defined length 14a of the overall conduit structure 14. Necessarily, length 14a must be substantially completely transparent to electromagnetic radiation at the operating frequency of the system. The inside of cavity section 18b is referred to herein as a sample zone. The axial length of this cavity section, measured generally between planes 44, 34 is about $0.375\lambda$, where $\lambda$ is the operating wave length of the system (at the frequency described) measured in a transmission medium having a dielectric constant of about 2.51.

One will recognize that, inasmuch as the interior of cavity section 18b is not homogenous, its apparent overall dielectric constant will result from the presence of the majority material, polystyrene, and the minority material, fluid within conduit length 14a. Experience has shown that, in the medical kind of applications specifically being illustrated herein, typical fluid within this conduit length will have a dielectric constant of about 50 (at 1600 MHz). Accordingly, with such a fluid presence, the "apparent" dielectric constant within cavity section 18b will be about 9. This dielectric constant is arrived at by simple averaging of the volume fractions contributed by the two key occupants of the interior of cavity 18b.

Cavity section 18c, formed at the right active side of lens 18a, is also cylindrical. It includes a central core 48 with a material such as the product known as STYCAST HiK 500F, sold by Emerson & Cuming, Canton, Mass., such material having a dielectric constant of about 9. The cavity section also includes an outer conductive layer 50. The reason for choosing a core having the dielectric constant mentioned is to balance the system, in the sense that, nominally, both of cavity sections 18b, 18c appear to be filled with substantially the same kind of material when fluid with a dielectric constant of about 50 is within conduit length 14a.

In the embodiment of the apparatus now being described, electrode 20 has the configuration illustrated in perspective in FIG. 3. Thus, this electrode includes a substantially full-circular ring section from which extend output conductors, one extending from the perimetral edge of the ring, and the other extending substantially from the center of revolution of the ring. It is these output conductors that are coupled, and as is illustrated schematically in FIG. 1, to an input in monitor circuitry 22.

Electrode 20 is suitably mounted within cavity section 18c with its circular portion lying in a plane 52 which is spaced from ring 30 by a distance of about 0.5λ, where λ is the operating wave length of the system at the frequency mentioned when considered within a transmission medium having a dielectric constant of about 9.0. The overall axial length of cavity section 18c, measured between plane 36 and a plane 54 is about the same as the axial length of cavity section 18b.

Figure 5:
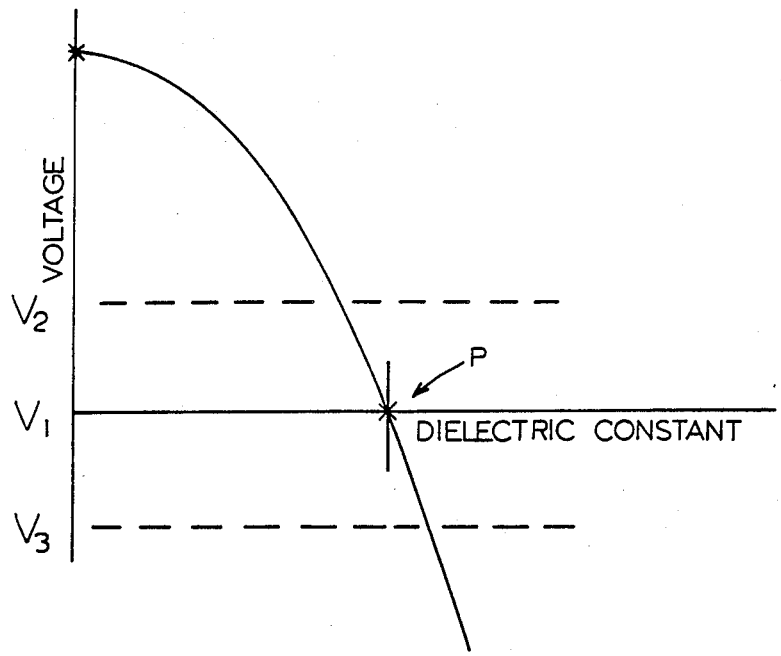
FIG. 5 is a calibration-derived curve of voltage (vertical scale) versus dielectric constant (horizontal scale).

Explaining a little more fully now the operation of the system thus described, let us now include reference to FIG. 5 which, as mentioned earlier, is a calibration-derived curve of voltage versus dielectric constant. As is certainly implied by the statement just made, the curve illustrated in FIG. 5 is derived through a conventional calibration technique involving monitoring voltage-amplitude output signals from electrode 20 as the dielectric constant of fluid contained in conduit length 14a is changed over a desired range. The parameters of the present system have been chosen so that the monitored output voltage $V_1$, which occurs with a fluid that creates the impression of an overall dielectric constant of 9 in cavity section 18b, coincides with point P in FIG. 5—this voltage $V_1$ lying generally centrally between two other voltages, $V_2$, $V_3$, which are chosen to define what might be thought of as a safety window. This safety window defines safe limits for operation of the intravenous transfer action of the system. In other words, voltages outside this window reflect a danger situation vis-a-vis the fluid then present is defined length 14a. Preferably, the parameters of the system, again through employing precalibration, are selected so that this safety window embraces a relatively linear stretch of the calibration curve.

Monitor circuitry 22, employing the calibration curve just described, produces a suitable output indication to indicate the dielectric-constant parameter of fluid within conduit length 14a, thus to allow medical personnel to monitor intravenous flow activity. The monitor circuitry can, of course, be provided to respond in a variety of ways should the safety window limits be breached, as for example by sounding an alarm, shutting down flow, etc.

FIG. 6B, which illustrates a plot of voltage-amplitude versus time, illustrates, at one region, a gradual shift (upwardly) in the amplitude of the voltage monitored in electrode 20, thus indicating a related shift in the dielectric-constant parameter of fluid within conduit length 14a.

Figure 6:
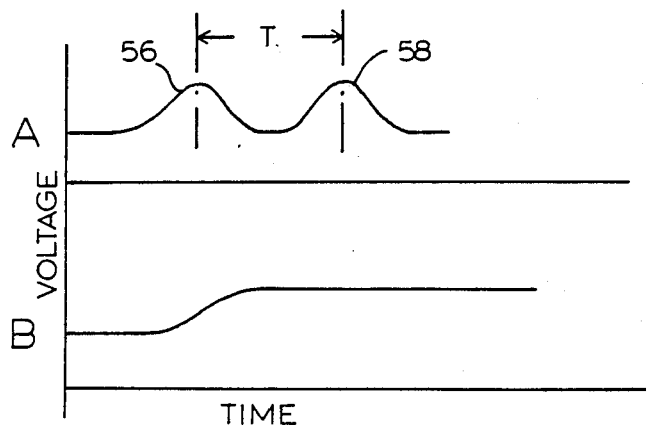
FIG. 6 is a graph illustrating two different waveforms (A and B)—waveform A being a plot of voltage (vertical scale) versus time (horizontal scale) from which fluid flow-rate can be determined, and waveform B illustrating voltage versus time from which a change in the material characteristic of fluid flowing in the system can be detected.

FIG. 6A, also a plot of voltage-amplitude versus time, helps to illustrate how rate of flow can be determined. To measure flow rate, a fluid, having an appreciably different dielectric constant than that currently being monitored, is injected on the upstream side of conduit length 14a. What has been referred to earlier herein as the wave front of this new fluid will, on entering cavity section 18b produce a "peak", such as that shown at 56 in FIG. 6A, in the voltage output from electrode 20. For the purpose of this illustration, the fluid chosen to be injected is the same as that flowing but at a higher temperature which creates a change in dielectric constant sufficient to produce a "positive" voltage peak. As this wave front exits cavity section 18b, its exit will produce another peak, such as the one shown at 58 in FIG. 6. These peaks are readily detectible because of the conscious choice, in the design of the apparatus of the invention, to place conduit length 14a closely adjacent the left active side of lens 18a and the volume of injected fluid which is known to be approximately 10 microliters. Knowledge of the time T (shown in FIG. 6) which exists between the high points of peaks 56, 58, along with knowledge of length L, enables simple computation of flow rate.

Figure 4:
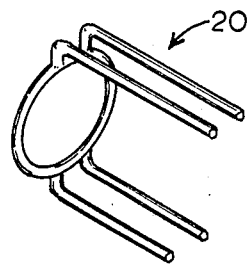

Considering now last of all FIG. 4, here electrode 20 is shown with a slightly different construction. This electrode includes a substantially complete ring portion, from opposite (upper and lower) diametral sides there extend two pairs of output conductors. Electrode 20, as depicted in FIG. 4, is mounted in cavity section 18c with the ring portion depressed as previously described, and with the two diametrically opposed pairs of output conductors each lying generally in the plane of FIG. 2. Put another way, a diametral line extending between these two pairs of terminals would lie substantially in the same plane as conduit length 14a.

With a FIG. 4-type electrode, the overall system is a bit more sensitive to the time-spaced voltage peaks which result from fluid injection to determine fluid-flow rate.

Thus, a non-perturbing cavity method and apparatus for measuring parameters, such as dielectric constant and flow rafe, of fluid within a conduit has been described.

Various features and advantages which are offered by the invention should be readily apparent to those skilled in the art. Naturally, variations and modifications may be made to suit different specific applications, all of which will come within the scope of, and without departing from the spirit of, the invention.

It is claimed and desired to secure by Letters Patent:

1. A method of measuring certain parameters of a fluid within a conduit, including such parameters as dielectric constant and flow rate, the method being non-perturbing to the fluid, comprising the steps of:
    positioning a defined length of the conduit within a resonant cavity, the cavity including a bidirectionally radiating lens therein having a pair of foci on opposite sides of the lens,
    directing electromagnetic energy from the bidirectionally radiating lens toward one focus thereof on one side of the lens including directing the electromagnetic energy into the defined length of conduit, and
    observing voltage-amplitude conditions over time on the opposite side of the lens at at least one monitoring site within the resonant cavity adjacent the other focus of the lens, whereby dielectric constant and flow-rate conditions of fluid within the defined length of the conduit can be selectively derived.

2. The method of claim 1 including the step of providing separate cores of solid materials in two zones of the cavity, one zone immediately surrounding the defined length of conduit on one side of the lens and the other zone immediately surrounding the at least one monitoring site on the opposite side of the lens, including providing solid materials having nominal dielectric constants which are substantially the same in both said zones.

3. The method of claim 1 in which the step of observing voltage-amplitude conditions over time includes monitoring an electromagnetic signal emanating from an electrode at the at least one monitoring site within the resonant cavity, the signal being composed of the incident wave from the bidirectionally radiating lens added to a reflected wave arriving from the zone of the cavity immediately surrounding the defined length of conduit on the side of the lens opposite the monitoring site.

4. The method of claim 1 in which the step of positioning a defined length of the conduit within a resonant cavity includes positioning a defined length of the conduit within a resonant cavity which is a body of revolution centered about an axis having openings at opposite sides and an overall length of slightly more than one-quarter of the operating wave length of the lens at a frequency of 1624-MHz and a dielectric constant of about 2.51, the step of directing the electromagnetic energy from the lens toward one focus includes directing electromagnetic energy from the lens toward one focus within a cavity section having an axial length of about 0.375 of the operating wave length of the lens at a frequency of 1624-MHz and a dielectric constant of about 2.51, and said step of observing voltage-amplitude conditions includes observing voltage-amplitude conditions at a location spaced from the center of the lens a distance of about one-half of the operating wave length of the lens at a frequency of 1624-MHz and a dielectric constant of about 2.51.

5. Apparatus for measuring certain selected parameters of a fluid within a conduit by means which are non-perturbing to the fluid, comprising:
   a resonant cavity adapted to receive a defined length of the conduit,
   bidirectional radiator means forming a portion of said cavity for directing electromagnetic energy into said defined length of the conduit on one side of said cavity and into a monitoring zone in said cavity on the opposite side of said cavity,
   means in said monitoring zone responsive to electromagnetic energy arriving at said monitoring zone, including electromagnetic energy reflected from the zone of said cavity immediately surrounding the defined length of the conduit, for generating signal information from said electromagnetic energy arriving at said monitoring zone, and
   means responsive to said signal information for generating, from the signal information, representations of the certain selected parameters.

6. Apparatus as in claim 5 in which the fluid in the conduit in selected applications will have a known dielectric constant when selected parameters are in a desired range, the apparatus including a core of solid material in the zone immediately surrounding the defined length of the conduit on the one side of said cavity and a core of solid material in said monitoring zone on the opposite side of said cavity, and in which the average dielectric constant of said zone immediately surrounding the defined length of the conduit, arrived at by averaging the volume fractions contributed by the fluid in said defined length of the conduit and said core of solid material in said zone, is approximately equal to the dielectric constant of said core of solid material in said monitoring zone.

7. Apparatus for measuring certain parameters of fluid within a conduit, including such parameters as dielectric constant and flow rate, by means which are non-perturbing to the fluid, comprising:
   means defining a resonant cavity, including a sample zone at one end of the cavity adapted to receive a defined length of a fluid-containing conduit, and a monitoring zone at the opposite end of the cavity containing a monitoring receiver at a monitoring site within said monitoring zone,
   a bidirectionally radiating lens having a pair of foci, said lens being disposed within and at least partially forming a central portion of said cavity, one said focus being on an active side of said lens disposed adjacent said sample zone and the other said focus being on an opposite active side of said lens disposed adjacent said monitoring zone, and
   means operatively connected to said monitoring receiver, operable with operation of said lens, and with a fluid-containing conduit extending within said sample zone, to produce output data from which, over time, the dielectric constant and flow rate of fluid within the conduit's defined length can be determined.

8. Apparatus as in claim 7 in which said lens has an overall length of slightly more than one-quarter of the operating wave length of the lens at a frequency of 1624-MHz and a dielectric constant of about 2.51, said sample zone is in a cavity section having an axial length of about 0.375 of the operating wave length of the lens at a frequency of 1624-MHz and a dielectric constant of about 2.51, and said monitoring receiver in said monitoring zone is spaced from the center of the lens a distance of about one-half of the operating wave length of the lens at a frequency of 1624-MHz and a dielectric constant of about 2.51.

* * * * *